(12) United States Patent
Bian et al.

(10) Patent No.: US 11,007,190 B2
(45) Date of Patent: *May 18, 2021

(54) SMART BROADCAST DEVICE

(71) Applicant: Advanced New Technologies Co., Ltd., Grand Cayman (KY)

(72) Inventors: Ran Bian, Hangzhou (CN); Huanmi Yin, Hangzhou (CN); Le Zhou, Hangzhou (CN)

(73) Assignee: Advanced New Technologies Co., Ltd., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 16/945,551

(22) Filed: Jul. 31, 2020

(65) Prior Publication Data

US 2020/0360369 A1 Nov. 19, 2020

Related U.S. Application Data

(63) Continuation of application No. 16/697,882, filed on Nov. 27, 2019, now Pat. No. 10,828,295, which is a
(Continued)

(30) Foreign Application Priority Data

Aug. 15, 2017 (CN) .......................... 201721023382.5

(51) Int. Cl.
G06K 5/00 (2006.01)
A61K 31/485 (2006.01)
(Continued)

(52) U.S. Cl.
CPC .......... *A61K 31/485* (2013.01); *A61K 9/0053* (2013.01); *A61K 9/50* (2013.01);
(Continued)

(58) Field of Classification Search
CPC ........... G06Q 20/3274; G06Q 20/3272; G06Q 20/3276; G06Q 20/385; G06Q 20/20;
(Continued)

(56) References Cited

U.S. PATENT DOCUMENTS 7,716,082 B1 * 5/2010 Blalock ................ G06Q 20/327
705/17
8,806,209 B2 8/2014 Hemphill et al.
(Continued)

FOREIGN PATENT DOCUMENTS

CN 101799902 8/2010
CN 103177516 6/2013
(Continued)

OTHER PUBLICATIONS

Crosby et al., "BlockChain Technology: Beyond Bitcoin," Sutardja Center for Entrepreneurship & Technology Technical Report, Oct. 16, 2015, 35 pages.
(Continued)

*Primary Examiner* — Thien M Le
(74) *Attorney, Agent, or Firm* — Fish & Richardson P.C.

(57) ABSTRACT

The present specification discloses a smart broadcast device, including: a device body, wherein the device body comprises a first surface that comprises a payment graphic code; a transceiver, installed inside the device body and configured to communicate with a payment service provider through maintaining a persistent wireless and/or wired network connection with the payment service provider; a processor, installed inside the device body and electrically connected to the transceiver; and a speaker, installed inside the device body and electrically connected to the processor, wherein the processor submits a payment result audio signal to the speaker upon receiving an external trigger signal from the payment service provider by using the transceiver, wherein
(Continued)

the external trigger signal includes data defining at least a portion of a payment result, and wherein the payment result audio signal drives the speaker to output payment result audio.

10 Claims, 6 Drawing Sheets

Related U.S. Application Data continuation of application No. PCT/CN2018/099558, filed on Aug. 9, 2018.

(51) Int. Cl.
*A61K 9/00* (2006.01)
*A61K 9/50* (2006.01)
*G06Q 20/32* (2012.01)
*A61K 31/4458* (2006.01)
*G06Q 20/20* (2012.01)
*A61K 31/135* (2006.01)

(52) U.S. Cl.
CPC ........ *A61K 31/135* (2013.01); *A61K 31/4458* (2013.01); *G06Q 20/209* (2013.01); *G06Q 20/3276* (2013.01); *G06Q 20/3278* (2013.01)

(58) Field of Classification Search
CPC ............. G06Q 20/322; G06Q 20/3278; G06Q 20/40145; G06F 21/32; G06F 3/0416; G06F 3/16
See application file for complete search history.

(56) References Cited

U.S. PATENT DOCUMENTS

| | | | |
|---|---|---|---|
| 2002/0095333 A1 | 7/2002 | Jokinen et al. | |
| 2010/0066677 A1 | 3/2010 | Garrett et al. | |
| 2011/0258121 A1 | 10/2011 | Kauniskangas et al. | |
| 2013/0191199 A1 | 7/2013 | Corner | |
| 2013/0232017 A1 | 9/2013 | Nathanel et al. | |
| 2013/0297422 A1 | 11/2013 | Hunter et al. | |
| 2014/0108252 A1* | 4/2014 | Itwaru ................ | G06Q 20/3276 705/44 |
| 2014/0117075 A1* | 5/2014 | Weinblatt ............... | G06Q 20/20 235/375 |
| 2014/0201069 A1 | 7/2014 | Arentz | |
| 2014/0276143 A1 | 9/2014 | Corl | |
| 2014/0279530 A1* | 9/2014 | Douglas ............. | G06Q 20/3274 705/44 |
| 2015/0011268 A1 | 1/2015 | Charugundla | |
| 2015/0089675 A1 | 3/2015 | Gulick | |
| 2015/0142654 A1 | 5/2015 | Zamer et al. | |
| 2015/0228044 A1 | 8/2015 | Jinno et al. | |
| 2015/0271150 A1 | 9/2015 | Barnett et al. | |
| 2016/0042485 A1* | 2/2016 | Kopel .................... | G07C 9/215 705/13 |
| 2016/0132864 A1* | 5/2016 | Barrese ............. | G06O 20/3224 382/190 |
| 2016/0162876 A1 | 6/2016 | Grigg | |
| 2016/0260077 A1* | 9/2016 | Hwang ............. | G06Q 20/3563 |
| 2016/0342974 A1 | 11/2016 | Feng et al. | |
| 2017/0004484 A1 | 1/2017 | Seol et al. | |
| 2017/0193543 A1 | 7/2017 | Priebatsch | |
| 2017/0323297 A1* | 11/2017 | Shanmugam ........ | G06Q 20/223 |
| 2018/0146078 A1* | 5/2018 | Shin ....................... | A45C 11/00 |
| 2018/0218370 A1 | 8/2018 | Denton | |
| 2018/0240123 A1 | 8/2018 | Jin et al. | |
| 2018/0247296 A1 | 8/2018 | Win et al. | |
| 2018/0330146 A1 | 11/2018 | Wang et al. | |
| 2018/0336384 A1 | 11/2018 | Maezawa et al. | |
| 2019/0251548 A1* | 8/2019 | Chen ................... | G06Q 20/388 |
| 2020/0051046 A1 | 2/2020 | Wang et al. | |
| 2020/0097946 A1 | 3/2020 | Bian et al. | |
| 2020/0111117 A1 | 4/2020 | Xiao et al. | |

FOREIGN PATENT DOCUMENTS

| | | |
|---|---|---|
| CN | 103402177 | 11/2013 |
| CN | 104469886 | 3/2015 |
| CN | 204242237 | 4/2015 |
| CN | 104599113 | 5/2015 |
| CN | 104660401 | 5/2015 |
| CN | 104794614 | 7/2015 |
| CN | 105117926 | 12/2015 |
| CN | 105117945 | 12/2015 |
| CN | 204856594 | 12/2015 |
| CN | 106296164 | 1/2017 |
| CN | 106296308 | 1/2017 |
| CN | 106303628 | 1/2017 |
| CN | 106447327 | 2/2017 |
| CN | 106779676 | 5/2017 |
| CN | 106845973 | 6/2017 |
| CN | 106886893 | 6/2017 |
| CN | 106886912 | 6/2017 |
| CN | 107423974 | 12/2017 |
| CN | 107480965 | 12/2017 |
| CN | 207148815 | 3/2018 |
| EP | 3154014 | 4/2017 |
| JP | 2013017157 | 8/2015 |
| JP | 2015148853 | 8/2015 |
| JP | 2016170697 | 9/2016 |
| JP | 6127179 | 5/2017 |
| TW | 201344603 | 11/2013 |
| TW | 201516911 | 5/2015 |
| TW | 201525896 | 7/2015 |
| WO | WO 2015062232 | 5/2015 |
| WO | WO 2015062255 | 5/2015 |
| WO | WO 2017075238 | 5/2017 |

OTHER PUBLICATIONS

Extended European Search Report in European Application No. 18845524.0, dated Mar. 31, 2020, 8 pages.
Extended European Search Report in European Application No. 18846757.5, dated Jun. 5, 2020, 9 pages.
Nakamoto, "Bitcoin: A Peer-to-Peer Electronic Cash System," www.bitcoin.org, 2005, 9 pages.
PCT International Preliminary Report on Patentability in International Application No. PCT/CN2018099555, dated Feb. 18, 2020, 10 pages (with partial English Translation).
PCT International Preliminary Report on Patentability in International Application No. PCT/CN2018099558, dated Feb. 18, 2020, 9 pages (with partial English Translation).
PCT International Search Report and Written Opinion in International Application No. PCT/CN2018/099555, dated Sep. 20, 2018, 9 pages (with partial English translation).
PCT International Search Report and Written Opinion in International Application No. PCT/CN2018/099558, dated Nov. 14, 2018, 9 pages (with partial English Translation).
PCT International Search Report and Written Opinion in International Application No. PCT/CN2018/103731, dated Nov. 23, 2018; 10 pages.
U.S. Appl. No. 16/598,686, filed Oct. 10, 2019, Linqing Wang.
U.S. Appl. No. 16/702,829, filed Dec. 4, 2019, Nan Xiao.

* cited by examiner

SMART BROADCAST DEVICE

CROSS-REFERENCE TO RELATED APPLICATIONS

This application is a continuation of and claims the benefit of priority of U.S. patent application Ser. No. 16/697,882, filed Nov. 27, 2019, which is a continuation of PCT Application No. PCT/CN2018/099558, filed on Aug. 9, 2018, which claims priority to Chinese Patent Application No. 201721023382.5, filed on Aug. 15, 2017, and each application is hereby incorporated by reference in their entirety.

TECHNICAL FIELD

The present specification relates to the field of smart hardware technologies, and in particular, to a smart broadcast device.

BACKGROUND

With the rapid development of Internet technologies, electronic transactions enter people's life. Online electronic transactions such as online transfer and online payment are gradually performed offline. For example, after purchasing an article or a service from a physical merchant, a user pays a bill over the Internet. In an offline electronic transaction scenario, a more timely and reliable transaction result feedback solution is needed.

SUMMARY

In view of this, the present specification provides a smart broadcast device.

The present specification is implemented by using the following technical solutions:

A smart broadcast device, including: a device body, where the device body includes a first surface that includes a payment graphic code; a communication module, installed inside the device body and communicating with outside through a wireless link and/or a wired link; a processing module, installed inside the device body and electrically connected to the communication module; and a speaker, installed inside the device body and electrically connected to the processing module, where the processing module outputs a payment result audio signal to the speaker when receiving an external trigger signal by using the communication module, to drive the speaker to output payment result audio.

Optionally, the first surface includes a display screen, configured to display the payment graphic code.

Optionally, a code layer of the payment graphic code is attached to the first surface.

Optionally, the device body further includes a lower surface, and an angle between the first surface and the lower surface is less than 90 degrees.

Optionally, the angle between the first surface and the lower surface is from 20 degrees to 70 degrees.

Optionally, speaker holes of the speaker are distributed on the left and right sides of the payment graphic code on the first surface.

Optionally, the smart broadcast device further includes: a USB interface, installed on the device body and configured to output power to charge an end-user device.

Optionally, the smart broadcast device further includes: an LED status indicator, installed on the device body and configured to output a corresponding light prompt based on a light drive signal output by the processing module.

Optionally, the smart broadcast device further includes a volume adjustment button.

Optionally, the smart broadcast device further includes: a Wi-Fi probe module, installed inside the device body and configured to detect end-user device information, where the processing module is further configured to encapsulate, according to a predetermined protocol, the end-user device information that is detected by the Wi-Fi module, and report the end-user device information by using the communication module.

Optionally, the smart broadcast device further includes: an NFC module, installed inside the device body and configured to: when detecting an end-user device with an NFC function, send information included in the payment graphic code to the end-user device by using an NFC technology.

It can be seen from the previous description that the smart broadcast device described in the present specification integrates the payment graphic code and a payment result broadcast function, a user can make a payment by scanning the payment graphic code included on the device body, and the processing module of the smart broadcast device can receive a trigger signal from a payment system by using the communication module, and output a payment result audio signal to the loudspeaker, to drive the loudspeaker to output payment result audio. As such, a payment result can be broadcasted in a timely and reliable way, and electronic payment experience can be improved. In addition, a brand effect of the payment system can be improved, which helps publicize the payment system.

DESCRIPTION OF IMPLEMENTATIONS

Example implementations are described in detail here, and implementations are presented in the accompanying drawings. When the following description relates to the accompanying drawings, unless specified otherwise, same numbers in different accompanying drawings represent same or similar elements. The implementations described in the following example implementations do not represent all implementations consistent with the present specification. On the contrary, the implementations are only examples of apparatuses and methods that are described in the appended claims in detail and consistent with some aspects of the present specification.

The terms used in the present specification are merely used for the purpose of describing specific implementations, and are not intended to limit the present specification. The terms "a", and "the" in singular forms used in the present specification and the appended claims are also intended to include plural forms, unless clarified in the context. It should be further understood that the term "and/or" used in the present specification indicates and includes any or all possible combinations of one or more related listed items.

It should be understood that although terms such as first, second, and third can be used in the present specification to describe various types of information, the information is not limited to these terms. These terms are only used to differentiate information of a same type. For example, within the range of the present specification, first information can also be referred to as second information. Similarly, the second information can also be referred to as the first information. Depending on the context, for example, the word "if" used here can be explained as "while", "when", or "in response to determining".

The present specification provides a smart broadcast solution that can be implemented through cooperation between a payment system and a smart broadcast device. The payment system is usually a server or a server cluster deployed by a payment service provider. The smart broadcast device has an audio broadcast function.

Figure 1:
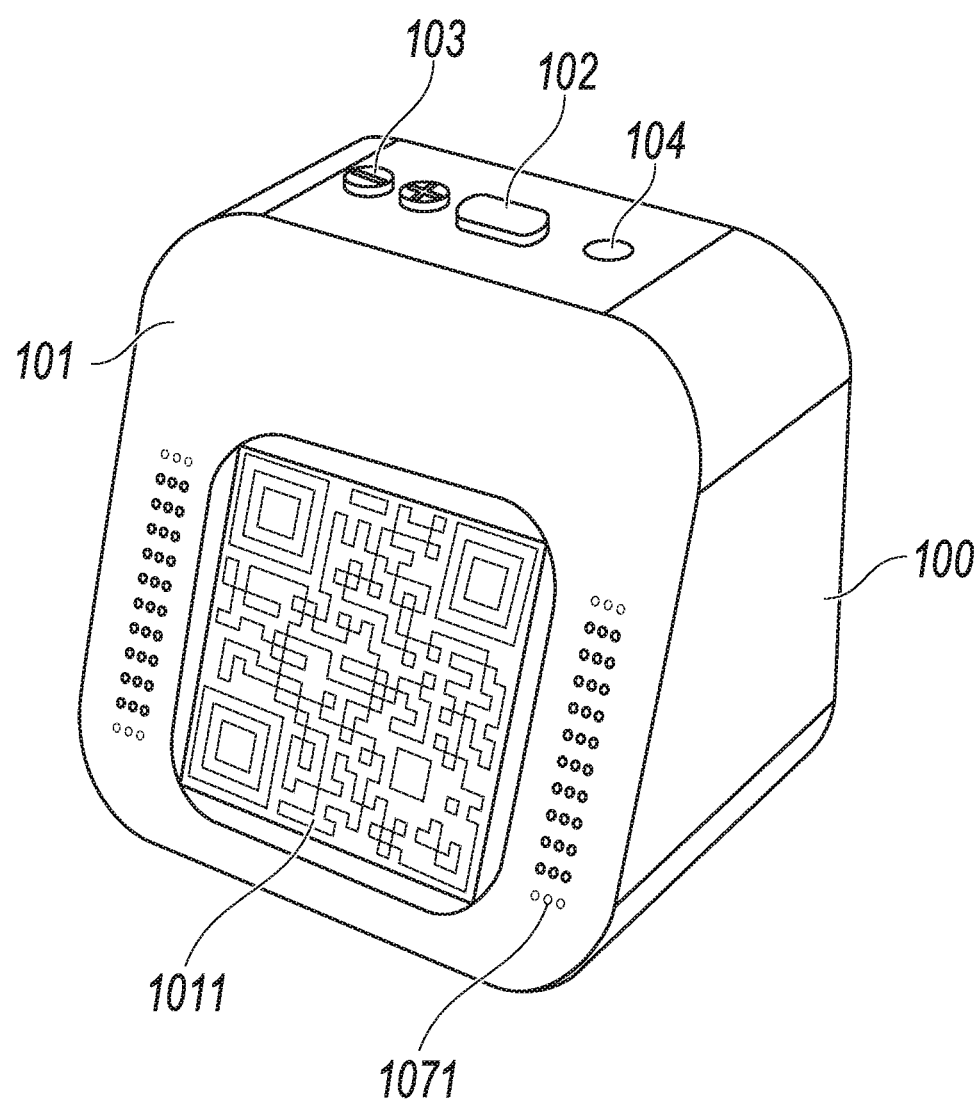
FIG. 1 is a schematic diagram illustrating a smart broadcast device, according to an example implementation of the present specification.

FIG. 1 is a schematic diagram illustrating a smart broadcast device, according to an example implementation of the present specification.

Referring to FIG. 1, the smart broadcast device includes a device body 100, and the device body 100 includes a first surface 101 including a payment graphic code 1011. The payment graphic code 1011 can include identification information of an account of a service provider. For example, the payment graphic code 1011 can include an identifier of a merchant account, and a user can scan the payment graphic code 1011 for payment. Or the payment graphic code 1011 can include a random code, a merchant can bind the payment graphic code 1011 to an account of the merchant, and subsequently, a user can scan the payment graphic code 1011 for payment. Implementations are not limited in the present specification.

In an example, a coding layer of the payment graphic code 1011 can be attached to the first surface 101. For example, the merchant prints the payment graphic code including the merchant account information, and then attaches the payment graphic code to the first surface 101.

In another example, the first surface 101 can include a display screen (not shown in the figure), configured to display the payment graphic code 1011. For example, after the smart broadcast device is bound to the merchant account, a payment system can send information related to the merchant account to the smart broadcast device, and the smart broadcast device can display the payment graphic code 1011 including the merchant account information on the display screen.

Certainly, in practice, the payment graphic code 1011 can be included in other methods. Implementations are not limited in the present specification.

Figure 2:
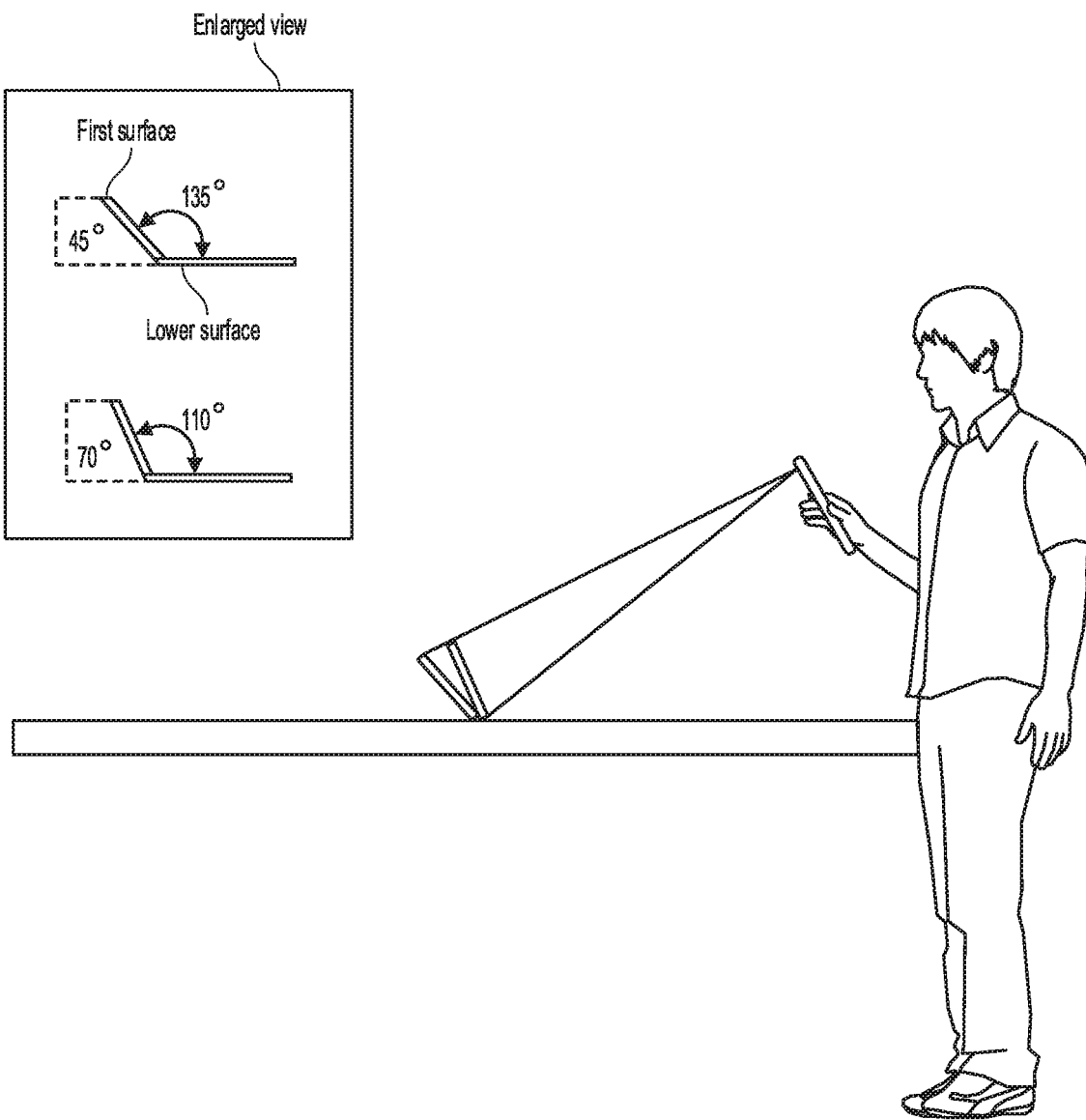
FIG. 2 is a schematic diagram illustrating scanning a payment graphic code on a smart broadcast device, according to an example implementation of the present specification.

In the present implementation, to help a user scan the payment graphic code 1011, an included angle between the first surface 101 and a lower surface of the device body can be set to be less than 90 degrees. Referring to FIG. 2, because height of a common desktop usually ranges from 70 cm to 1 m, to adapt to posture of using an end-user device such as a mobile phone when the user stands, the included angle between the first surface 101 and the lower surface of the device body can be set from 20 degrees to 70 degrees to help the user scan the payment graphic code 1011, and the user does not need to excessively adjust the posture of holding the mobile phone. As such, user experience can be improved.

Referring back to FIG. 1, the device body 100 of the smart broadcast device can be further provided with a power key (main control key) 102, a volume adjustment key 103, an LED status indicator 104, a USB interface (not shown in the figure), a power cable (not shown in the figure), etc. There are usually two volume adjustment keys 103: One key is configured to turn up the volume, and the other key is configured to turn down the volume. The USB interface can be located on a second surface (not shown in the figure) on the device body 100 opposite to the first surface 101 to output power for charging the end-user device such as the mobile phone. For example, the USB interface outputs power of 5V/1 A. The power cable can be used to connect to an alternating current of 220V, etc.

Alternatively, the power key 102, the volume adjustment key 103, and the LED status indicator 104 can be installed at another location on the device body 100. Implementations are not limited in the present specification.

Figure 3:
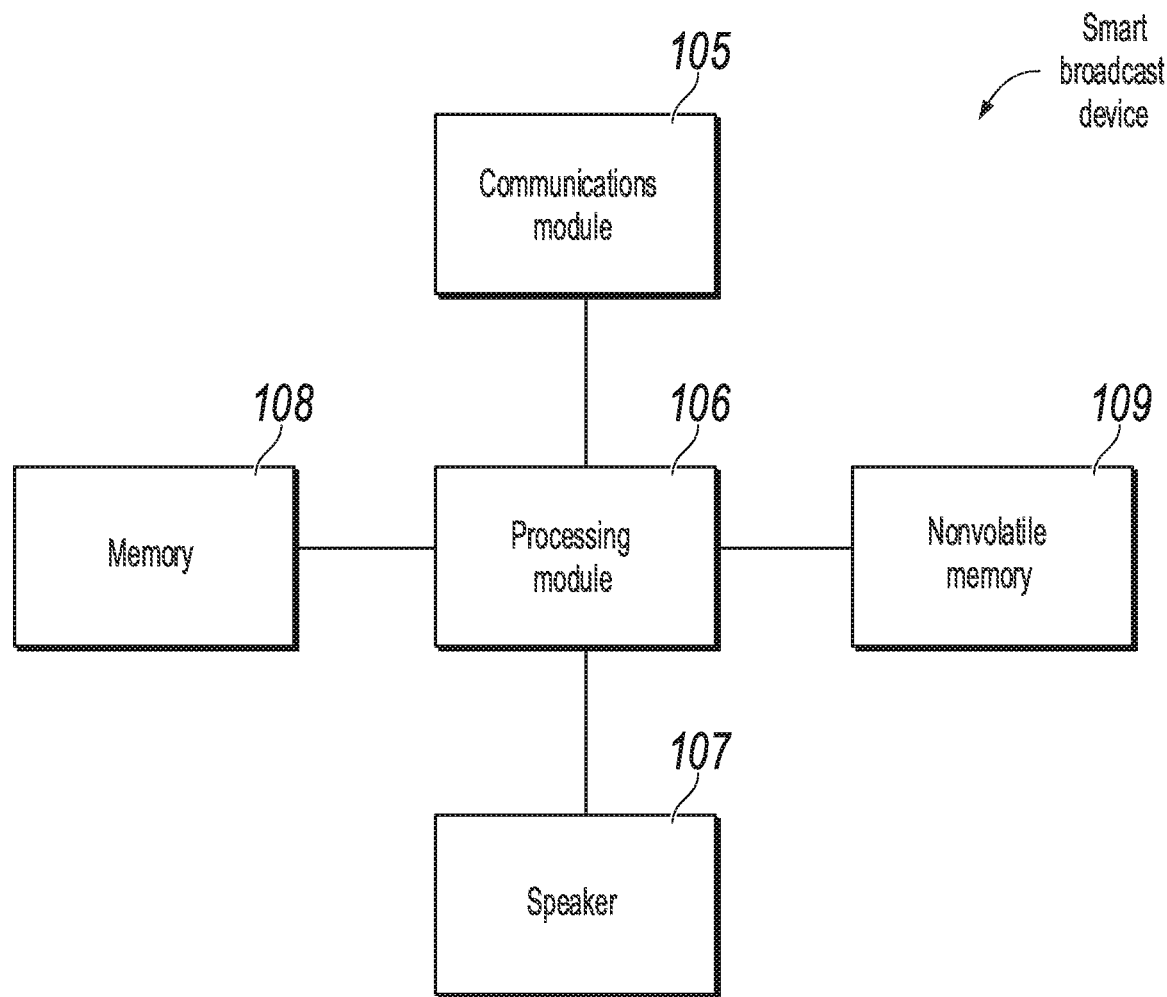
FIG. 3 is a schematic diagram illustrating another smart broadcast device, according to an example implementation of the present specification.

FIG. 3 is a schematic diagram illustrating another smart broadcast device, according to an example implementation of the present specification.

Based on the implementation shown in FIG. 1, referring to FIG. 3, the smart broadcast device can further include a communication module 105. The communication module 105 is installed inside the device body 100, and can communicate with outside through a wireless and/or a wired link. For example, the communication module 105 can be a Wi-Fi module, and can communicate with outside by using a Wi-Fi technology. For another example, the communication module 105 can be a Bluetooth module, and can communicate with outside by using a Bluetooth technology. Certainly, the communication module 105 can also be used as a general term of a module having a communication function, such as the Wi-Fi module and the Bluetooth module. Implementations are not limited in the present specification.

The smart broadcast device further includes a processing module 106. The processing module 106 is installed inside the device body 100, and can be electrically connected to the communication module 105. The processing module 106 can be a micro control unit (MCU), a CPU, a field-programmable gate array (FPGA), etc. Implementations are not limited in the present specification.

The smart broadcast device can further include a speaker 107. The speaker 107 can be installed inside the device body 100, and can be electrically connected to the processing module 106. In an example, referring back to FIG. 1, speaker holes 1071 of the speaker 107 can be distributed on left and right sides of the payment graphic code 1011 on the first surface 101. Certainly, the speaker holes 1071 of the speaker 107 can be alternatively distributed at another location of the device body 100. Implementations are not limited in the present specification.

The smart broadcast device can further include a memory 108, a nonvolatile memory 109, etc. Implementations are not limited in the present specification.

In the present implementation, for example, when a service provider is a merchant, the merchant can bind the smart broadcast device to a collection account of the merchant in advance. For example, the merchant can scan a device graphic code of the smart broadcast device by using a client that logs in based on the collection account; the client can obtain a unique hardware identifier of the device from the device graphic code through parsing, and then send a binding request including the hardware identifier and the collection account to a payment system; and the payment system stores a binding relationship between the hardware identifier and the collection account.

In the present implementation, after processing a payment request for the collection account, the payment system can send a trigger signal to the smart broadcast device based on the hardware identifier bound to the collection account. The processing module 106 of the smart broadcast device can receive the trigger signal from the payment system by using the communication module 105, and can further output a payment result audio signal to the speaker 107 to drive the speaker 107 to output payment result audio For example, ** RMB is successfully received.

It can be seen from the previous description that the smart broadcast device described in the present specification integrates the payment graphic code and a payment result broadcast function, the user can make a payment by scanning the payment graphic code included on the device body, and the processing module of the smart broadcast device can receive the trigger signal from the payment system by using the communication module, and output the payment result audio signal to the loudspeaker, to drive the loudspeaker to output the payment result audio. As such, a payment result can be broadcasted in a timely and reliable way, and electronic payment experience can be improved. In addition, a brand effect of the payment system can be improved, which helps publicize the payment system.

The following uses an example that the service provider is a merchant, to describe a specific implementation process of the present specification separately in terms of network configuration of the smart broadcast device, binding of the smart broadcast device, power-on of the smart broadcast device, and output of the payment result audio.

1. Network Configuration of the Smart Broadcast Device

In the present implementation, before the merchant uses the smart broadcast device, a network usually needs to be configured for the smart broadcast device to enable the smart broadcast device to access the Internet.

In the present implementation, the communication module 105 of the smart broadcast device includes a Wi-Fi module, and the Wi-Fi module supports a STA (Station) mode and an AP (Access Point) mode.

After the smart broadcast device is powered on, the merchant can switch the Wi-Fi module to the AP mode through triggering by a specified physical key. In the AP mode, the smart broadcast device serves as an access point, and can be allowed to connect to an end-user device. The specified physical key can be set by a developer. To alleviate an unintentional touch, two physical keys can be installed, for example, a power key and a volume (−) key.

A mobile phone is used as an example. The merchant can simultaneously press the power key and the volume (−) key to switch the Wi-Fi module to the AP mode; then select a service set identifier (SSID) of the smart broadcast device from a Wi-Fi list of the mobile phone; and enter a corresponding password, to establish a connection. The SSID and the corresponding password of the smart broadcast device can be pre-printed on a device body 100, for example, pre-printed on a lower surface of the device body 100 or another position.

After the mobile phone successfully accesses Wi-Fi of the smart broadcast device, the merchant can configure Wi-Fi connection information through the Wi-Fi connection, for example, an SSID and a password of a router. For example, after successfully accessing the Wi-Fi of the smart broadcast device, a client can display a message that the smart broadcast device is connected, and then the merchant can configure the SSID and password of the router for the smart broadcast device by using the client.

After the mobile phone successfully accesses Wi-Fi of the smart broadcast device, the merchant can configure Wi-Fi connection information by using the Wi-Fi connection, for example, an SSID and password of a router.

After accessing the Internet, the smart broadcast device can establish a persistent connection to the payment system based on a preconfigured address of the payment system, to receive various types of information sent by the payment system.

The address of the payment system is usually stored in the nonvolatile memory 109. A request packet for establishing a persistent connection is usually encapsulated by the processing module 106, and is usually sent and received by using the communication module 105.

An implementation procedure of each function is highlighted when each function of the smart broadcast device is subsequently described in the present specification. For a process in which hardware modules of the smart broadcast device cooperate to implement a corresponding function, references can be made to a related technology. Details are omitted in the present specification. For example, the processor 105 outputs an audio signal to a speaker, to drive the speaker to output corresponding audio, and this can be described as outputting corresponding audio by the smart broadcast device.

In another example, when a network of the smart broadcast device is configured, a Bluetooth connection can be first established to the smart broadcast device, and then Wi-Fi connection information is sent by using the Bluetooth connection, so that the smart broadcast device accesses the Internet. Implementations are not limited in the present specification.

2. Binding of the Smart Broadcast Device

In the present implementation, the device body 100 of the smart broadcast device usually can further include a device graphic code (not shown in the figure). The device graphic code includes a device identifier of the device, such as a unique hardware identifier.

The device graphic code is usually used only when the merchant binds the smart broadcast device. Therefore, the device graphic code can be provided on the lower surface of the device body 100. For example, the device graphic code is stuck to the lower surface of the device body. Certainly, the device graphic code can alternatively be located at another location of the device body, for example, a surface opposite to the first surface 101. Forms of the device graphic code can be a bar code, a two-dimensional code, etc. Implementations are not limited in the present specification.

The merchant needs to bind the smart broadcast device to the collection account of the merchant (which is referred to as a merchant account below) before using the smart broadcast device.

Figure 4:
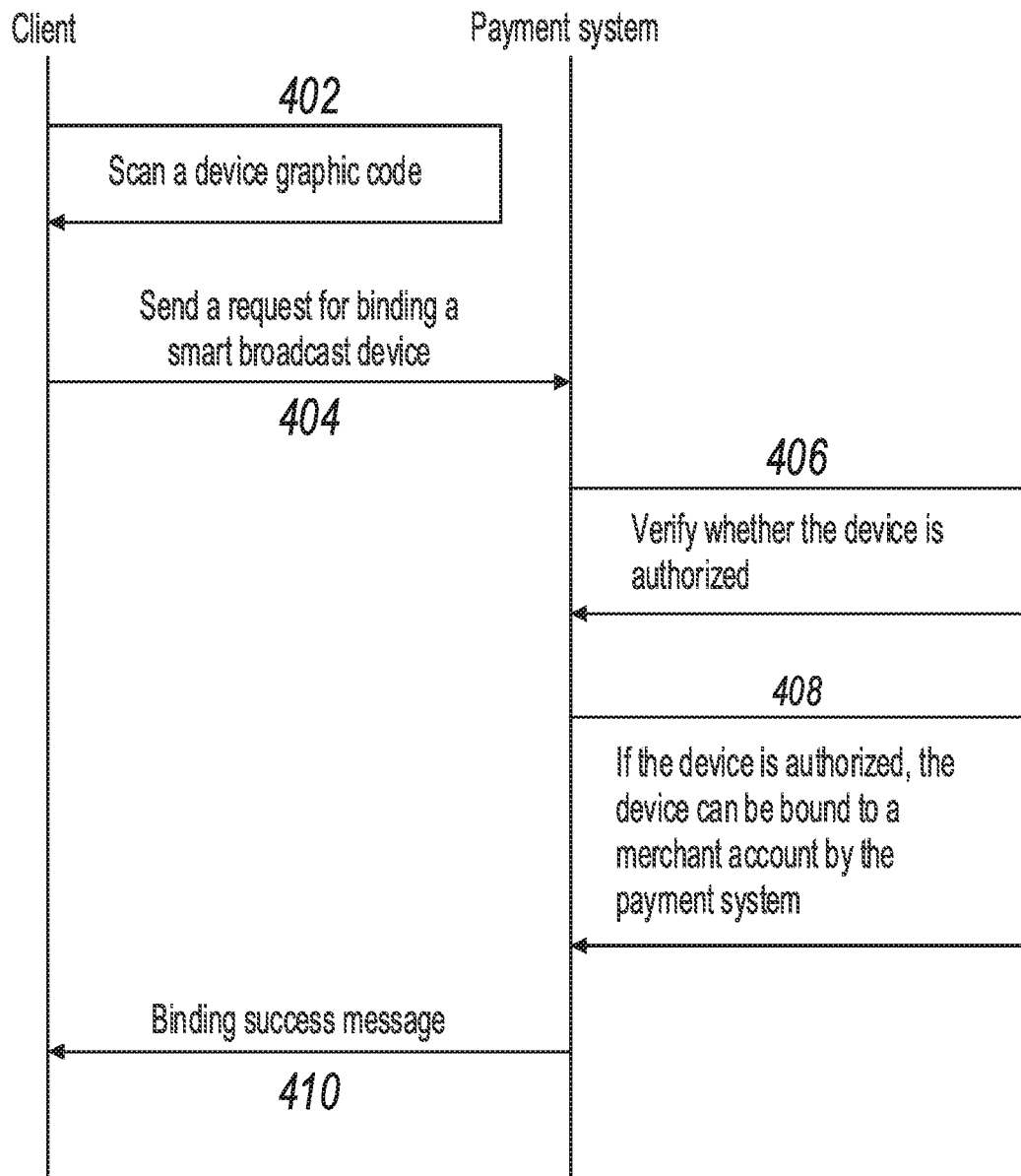
FIG. 4 is a schematic flowchart illustrating binding a smart broadcast device, according to an example implementation of the present specification.

In the present implementation, referring to FIG. 4, a process of binding the smart broadcast device can include the following steps.

Step 402: The client scans a device graphic code on the smart broadcast device.

A merchant can scan the device graphic code on the smart broadcast device by using a client that logs in based on a merchant account.

Step 404: The client sends, to the payment system, a request for binding a smart broadcast device.

After the scanning, the client can obtain a device identifier of the smart broadcast device, and then the client can send, to the payment system, the request for binding the broadcast device. The request includes the device identifier and the merchant account, for example, identification information of the merchant account.

Step 406: The payment system verifies whether the smart broadcast device is authorized.

After receiving the request for binding the broadcast device, the payment system can first verify, based on the device identifier, whether the corresponding smart broadcast device is authorized.

For example, the payment system can verify whether the smart broadcast device is authorized on a hardware platform that stores identifiers of authorized devices.

Certainly, the payment system can perform local verification if the payment system locally stores a list of identifiers of authorized devices. Implementations are not limited in the present specification.

In response to determining that the smart broadcast device is unauthorized, the payment system can return a security prompt to the client to remind the merchant of a security risk.

Step 408: In response to determining that the smart broadcast device is authorized, the payment system can bind the device identifier to the merchant account.

Step 410: The payment system returns a binding success message to the client.

In the present implementation, after binding the device identifier to the merchant account, the payment system can further check whether the corresponding smart broadcast device is online, in other words, check whether the corresponding smart broadcast device establishes a persistent connection to the payment system. In response to determining that the smart broadcast device is online, the payment system can further send the binding success message to the smart broadcast device, and the smart broadcast device can further output audio indicating that the user account is successfully bound.

The binding success audio can be general audio, for example, an account is successfully bound. The binding success audio can further include information about the merchant account, for example, A's account is successfully bound. The information about the merchant account is included in the binding success message sent by the payment system. Implementations are not limited in the present implementation.

In the present implementation, the merchant can view a status of the smart broadcast device by using the client, for example, whether the smart broadcast device is bound, and whether the bound smart broadcast device is online. For processing and implementation of this part, references can be made to a related technology. Details are omitted in the present implementation.

In the present implementation, the merchant can further unbind the smart broadcast device by using the client, for example, click an unbind button provided by a user page of the client; the client can further send an unbinding request to the payment system; and the payment system can further unbind the merchant account from the smart broadcast device. After the unbinding, the payment system can further send an unbinding message to the corresponding smart broadcast device, so that the smart broadcast device outputs unbinding prompt audio, for example, "unbinding succeeded".

Optionally, in another example, the payment system can further monitor whether the smart broadcast device is at a security risk, automatically unbind the smart broadcast device from the merchant account when determining that the smart broadcast device is at a security risk, and send a prompt to the client to protect interests of the merchant.

In this example, the smart broadcast device can periodically report device data of the device to the payment system. The device data can include an operating system version number, a speaker firmware number, etc. After receiving the device data, the payment system can determine, based on the device data, whether the smart broadcast device is at a security risk. For example, the payment system can determine whether the operating system version number is the latest, whether the speaker firmware number is correct, etc. In response to determining that the operating system version number is the latest and the speaker firmware number is correct, the payment system can determine that the corresponding smart broadcast device is not at a security risk; and in response to determining that the operating system version number is not the latest or the speaker firmware number is incorrect, the payment system can determine that the smart broadcast device is at a security risk. Certainly, in practice, the device data can further include other information, and a method that the payment system determines whether the smart broadcast device is at a security risk can be further extended based on the other information. Implementations are not limited in the present specification.

In this example, the payment system can confirm the security risk after receiving the device data. Or the payment system can first store the received device data, and then confirm the security risk offline when not busy. Implementations are not limited in the present specification.

3. Power-On of the Smart Broadcast Device

Figure 5:
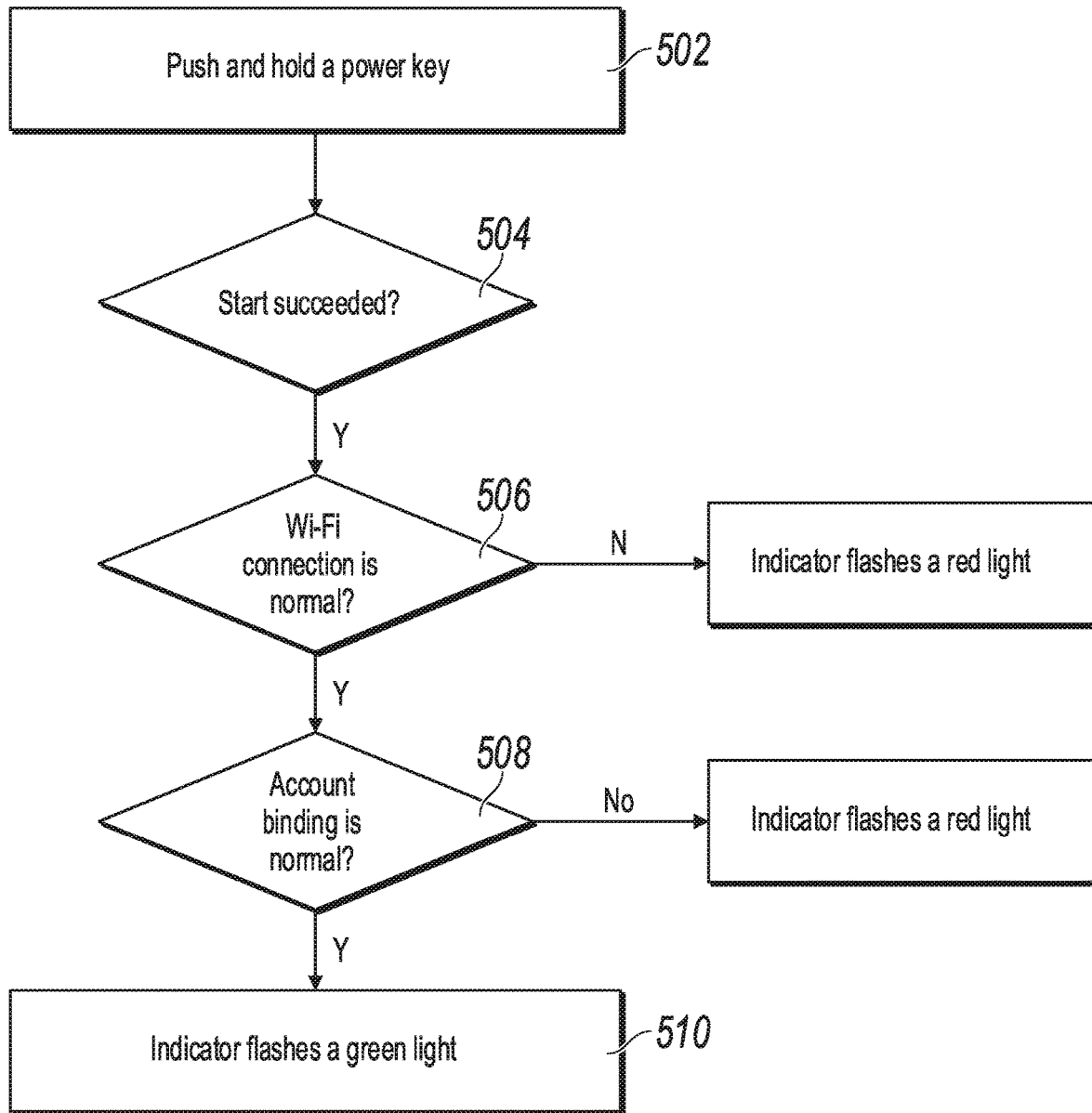
FIG. 5 is a schematic flowchart illustrating powering on a smart broadcast device, according to an example implementation of the present specification.

Referring to FIG. 5, a power-on procedure of the smart broadcast device in the present implementation can include the following steps.

Step 502: Push and hold the power key.

In the present implementation, the power key 102 of the smart broadcast device can be pushed and held for power-on, for example, pushed and held for three seconds.

Step 504: The smart broadcast device determines whether start succeeds, and performs step 506 in response to determining that the start succeeds.

In the present implementation, in response to determining that the start fails, the smart broadcast device can output a power-on failure sound.

Step 506: The smart broadcast device detects whether a Wi-Fi connection is normal, and performs step 508 in response to determining that the Wi-Fi connection is normal.

In the present implementation, an LED status indicator flashes a red light when the smart broadcast device starts for the first time because Wi-Fi connection information is not configured.

In the present implementation, after the Wi-Fi connection information is configured, the smart broadcast device can attempt to access a network based on the previously configured Wi-Fi connection information if the start succeeds, for example, attempt to access a router based on an SSID and a password of the router.

If the network is successfully connected, it can be determined that the Wi-Fi connection is normal, and step 508 is further performed.

If the network is unsuccessfully connected, the LED status indicator can be controlled to flash a red light to prompt a network access failure.

Step 508: The smart broadcast device detects whether account binding is normal, and performs step 510 in response to determining that the account binding is normal.

According to step 506, the smart broadcast device can establish a persistent connection to the payment system based on a stored address of the payment system if the Wi-Fi connection is normal, and can send a binding query request to the payment system after establishing the persistent connection, to query a binding status between the device and the merchant account. The binding query request can include the device identifier of the device.

After receiving the binding query request, the payment system can determine whether the smart broadcast device is bound to the merchant account, and return a query result to the smart broadcast device. The query result can be: bound or unbound.

If the bound query result is received, it can be determined that the account binding is normal, and then step 510 is further performed.

If the unbound query result is received, it can be determined that the account binding is abnormal, and then the LED status indicator can be controlled to flash a red light for prompting. When determining, based on the LED status indicator, that the account binding is abnormal, the merchant can check by using the client, to resolve binding abnormality in time, thereby alleviating a problem that payment result audio cannot be broadcasted due to the binding abnormality.

Step 510: Control the LED status indicator to flash a green light.

Based on the detection result in step 508, if the account binding is normal, it indicates that the smart broadcast device has entered a working state, so that the LED status indicator can flash a green light.

It is worthwhile to note that, in the present implementation, a light prompt that is output by the LED status indicator is only an example. In practice, another light prompt can be output. For example, the LED status indicator flashes a red light when the Wi-Fi connection is abnormal or the account binding is abnormal. Implementations are not limited in the present specification.

4. Output of the Payment Result Audio

Figure 6:
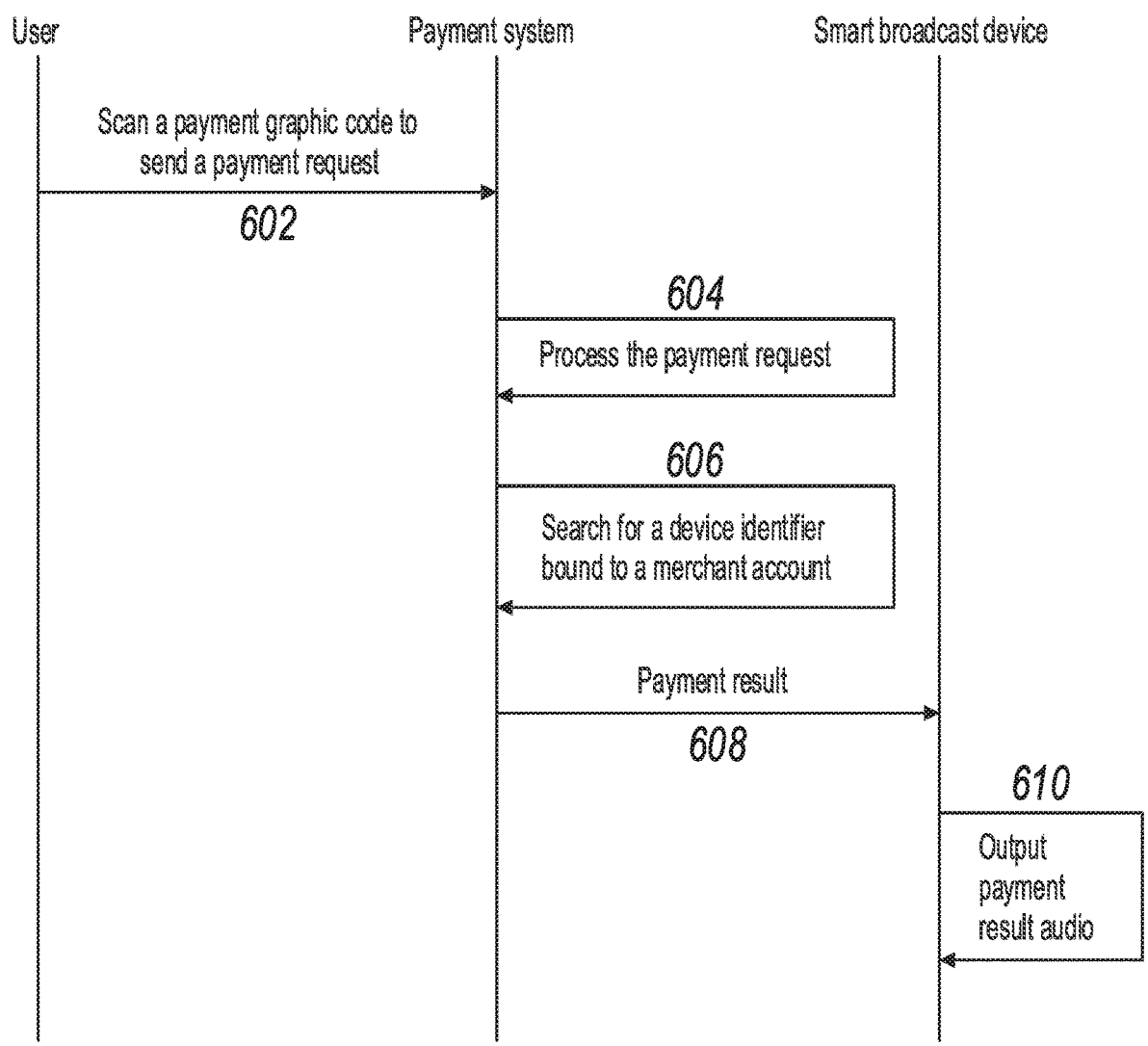
FIG. 6 is a schematic flowchart illustrating broadcasting payment result audio by a smart broadcast device, according to an example implementation of the present specification.

Referring to FIG. 6, the smart broadcast device can broadcast the payment result audio by using the following steps.

Step 602: A user scans the payment graphic code included in the body of the smart broadcast device.

In the present implementation, after the user performs consumption, the user can scan the payment graphic code such as a two-dimensional payment code included in the body of the smart broadcast device by using a client loaded in the mobile phone.

After scanning the payment graphic code, the client can display a payment page for a merchant account, and the user pays based on the payment page, for example, enters a consumption amount and confirms the payment.

After the user confirms the payment, the client can send a payment request to the payment system. The payment request usually includes information such as a payment amount, the merchant account, and time.

Optionally, in another example, the smart broadcast device can be further provided with a near field communication (NFC) module. When detecting an end-user device supporting an NFC technology, the NFC module can send information included in the payment graphic code to the end-user device by using the NFC technology. After receiving the information, the payment page for the merchant account can also be displayed for the user for payment. The information included in the payment graphic code can be sent by the payment system after the smart end-user device is bound to the merchant account.

In this example, the NFC module sends the information included in the payment graphic code, to effectively alleviate a scanning failure caused when the user does not align the payment graphic code during scanning. As such, a scanning success rate can be increased.

Optionally, in another example, the user can also pay by scanning a two-dimensional payment code provided by the merchant at another location. Implementations are not limited in the present specification.

Step 604: The payment system processes the payment request for the merchant account.

Step 606: After payment succeeds, the payment system searches for a device identifier of the smart broadcast device bound to the merchant account.

Step 608: The payment system sends a payment result to the corresponding smart broadcast device based on the identified device identifier.

Step 610: The smart broadcast device outputs the payment result audio.

In an example, the payment result sent by the payment system can be payment result audio, and the smart broadcast device can directly play the payment result audio after receiving the payment result audio.

In another example, because a data volume of the payment result audio is usually large, a relatively large bandwidth of the payment system can be occupied for transmitting the payment result audio, affecting performance of the payment system. Optionally, the payment result sent by the payment system can be a uniform resource locator (URL) of payment result audio. After receiving the URL sent by the payment system, the smart broadcast device can obtain the corresponding payment result audio from a corresponding address based on the URL, and then play the corresponding payment result audio. Unlike the way in which payment result audio is directly sent, this solution improves performance of the payment system.

In another example, to occupy fewer network resources and improve payment result transmission efficiency, the smart broadcast device can broadcast payment result audio in an audio combination way.

In detail, the smart broadcast device can pre-save basic audio in the payment result audio, for example, "successfully received" and "RMB". After payment succeeds, the payment result sent by the payment system to the smart broadcast device can be a payment result parameter, for example, a specific amount paid by the user.

After receiving the payment result parameter, the smart broadcast device can combine payment result audio based on the payment result parameter and the saved basic audio for broadcast.

For example, the user successfully pays 10 RMB. In this case, the payment system can send the payment result parameter 10, and after receiving the payment result parameter 10, the smart broadcast device can obtain the basic audio "successfully received" and "RMB", and then combine the payment result audio "10 RMB is successfully received" for broadcast.

In another example, when payment fails, the payment system can also send a payment result to the corresponding smart broadcast device, so that the smart broadcast device outputs corresponding payment result audio. Implementations are not limited in the present implementation.

It can be seen that after being bound to a merchant account, the smart broadcast device provided in the present specification can broadcast payment result audio specific to the merchant account, so that staff of the merchant can hear a payment result in a timely way. Unlike a smart speaker, the smart broadcast device is independent of an end-user device. When an end-user device that logs in based on the merchant account is not in a store, for example, when a storekeeper leaves the store with a mobile phone, the staff of the merchant can also hear the payment result, to protect interests of the merchant. In addition, according to the smart broadcast device provided in the present specification, a brand effect of the payment system can be improved, which helps publicize the payment system.

In another example, a Wi-Fi probe module can be further installed in the smart broadcast device, and can be configured to detect end-user device information, to assist the merchant in analyzing an operation status, for example, a passenger flow volume, the number of users, and the number of lost users.

The Wi-Fi probe module can report the detected information to the payment system. For example, the Wi-Fi probe module encapsulates the detected information according to a predetermined protocol, and then reports the detected information to the payment system. The detected information can include the number of end-user devices and device information of the end-user device, for example, a media access control (MAC) address.

After receiving the detected information, the payment system can perform user retention analysis, funnel analysis, etc. to assist the merchant in analyzing the operation status of the merchant, and can push an analysis result to the merchant.

Optionally, based on the Wi-Fi probe module, the payment system can further support the merchant in customizing audio push information.

For example, the merchant wants to carry out a promotion program that any user can get a coke for free if the user spends more than 50 RMB for purchased articles when there are 30 users in a store. The merchant can preset push information audio and a push condition of the program by using the client. The push condition is that there are 30 users in the store, and the push information audio can be "any user can get a coke for free if the user spends more than 50 RMB for purchased articles".

Based on the previous configuration, after receiving the detected information reported by the smart broadcast device, the payment system can determine whether the number of end-user devices that is included in the detected information reaches 30. If the number of end-user devices reaches 30, the payment system can determine that there are 30 users in the store, and then can send the push information audio configured by the merchant to the smart broadcast device, for example, a URL of the push information audio, so that the smart broadcast device broadcasts the push information audio.

In practice, the merchant can configure a large amount of push information audio and corresponding push conditions. Implementations are not limited in the present implementation.

The previous descriptions are merely preferred implementations of the present specification, but are not intended to limit the present specification. Any modification, equivalent replacement, or improvement made within the spirit and principle of the present specification shall fall within the protection scope of the present specification.

Embodiments and the operations described in this specification can be implemented in digital electronic circuitry, or in computer software, firmware, or hardware, including the structures disclosed in this specification or in combinations of one or more of them. The operations can be implemented as operations performed by a data processing apparatus on data stored on one or more computer-readable storage devices or received from other sources. A data processing apparatus, computer, or computing device may encompass apparatus, devices, and machines for processing data, including by way of example a programmable processor, a computer, a system on a chip, or multiple ones, or combinations, of the foregoing. The apparatus can include special purpose logic circuitry, for example, a central processing unit (CPU), a field programmable gate array (FPGA) or an application-specific integrated circuit (ASIC). The apparatus can also include code that creates an execution environment for the computer program in question, for example, code that constitutes processor firmware, a protocol stack, a database management system, an operating system (for example an operating system or a combination of operating systems), a cross-platform runtime environment, a virtual machine, or a combination of one or more of them. The apparatus and execution environment can realize various different computing model infrastructures, such as web services, distributed computing and grid computing infrastructures.

A computer program (also known, for example, as a program, software, software application, software module, software unit, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A program can be stored in a portion of a file that holds other programs or data (for example, one or more scripts stored in a markup language document), in a single file dedicated to the program in question, or in multiple coordinated files (for example, files that store one or more modules, sub-programs, or portions of code). A computer program can be executed on one computer or on multiple computers that are located at one site or distributed across multiple sites and interconnected by a communication network.

Processors for execution of a computer program include, by way of example, both general—and special-purpose microprocessors, and any one or more processors of any kind of digital computer. Generally, a processor will receive instructions and data from a read-only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data. A computer can be embedded in another device, for example, a mobile device, a personal digital assistant (PDA), a game console, a Global Positioning System (GPS) receiver, or a portable storage device. Devices suitable for storing computer program instructions and data include non-volatile memory, media and memory devices, including, by way of example, semiconductor memory devices, magnetic disks, and magneto-optical disks. The processor and the memory can be supplemented by, or incorporated in, special-purpose logic circuitry.

Mobile devices can include handsets, user equipment (UE), mobile telephones (for example, smartphones), tablets, wearable devices (for example, smart watches and smart eyeglasses), implanted devices within the human body (for example, biosensors, cochlear implants), or other types of mobile devices. The mobile devices can communicate wirelessly (for example, using radio frequency (RF) signals) to various communication networks (described below). The mobile devices can include sensors for determining characteristics of the mobile device's current environment. The sensors can include cameras, microphones, proximity sensors, GPS sensors, motion sensors, accelerometers, ambient light sensors, moisture sensors, gyroscopes, compasses, barometers, fingerprint sensors, facial recognition systems, RF sensors (for example, Wi-Fi and cellular radios), thermal sensors, or other types of sensors. For example, the cameras can include a forward- or rear-facing camera with movable or fixed lenses, a flash, an image sensor, and an image processor. The camera can be a megapixel camera capable of capturing details for facial and/or iris recognition. The camera along with a data processor and authentication information stored in memory or accessed remotely can form a facial recognition system. The facial recognition system or one-or-more sensors, for example, microphones, motion sensors, accelerometers, GPS sensors, or RF sensors, can be used for user authentication.

To provide for interaction with a user, embodiments can be implemented on a computer having a display device and an input device, for example, a liquid crystal display (LCD) or organic light-emitting diode (OLED)/virtual-reality (VR)/augmented-reality (AR) display for displaying information to the user and a touchscreen, keyboard, and a pointing device by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments can be implemented using computing devices interconnected by any form or medium of wireline or wireless digital data communication (or combination thereof), for example, a communication network. Examples of interconnected devices are a client and a server generally remote from each other that typically interact through a communication network. A client, for example, a mobile device, can carry out transactions itself, with a server, or through a server, for example, performing buy, sell, pay, give, send, or loan transactions, or authorizing the same. Such transactions may be in real time such that an action and a response are temporally proximate; for example an individual perceives the action and the response occurring substantially simultaneously, the time difference for a response following the individual's action is less than 1 millisecond (ms) or less than 1 second (s), or the response is without intentional delay taking into account processing limitations of the system.

Examples of communication networks include a local area network (LAN), a radio access network (RAN), a metropolitan area network (MAN), and a wide area network (WAN). The communication network can include all or a portion of the Internet, another communication network, or a combination of communication networks. Information can be transmitted on the communication network according to various protocols and standards, including Long Term Evolution (LTE), 5G, IEEE 802, Internet Protocol (IP), or other protocols or combinations of protocols. The communication network can transmit voice, video, biometric, or authentication data, or other information between the connected computing devices.

Features described as separate implementations may be implemented, in combination, in a single implementation, while features described as a single implementation may be implemented in multiple implementations, separately, or in any suitable sub-combination. Operations described and claimed in a particular order should not be understood as requiring that the particular order, nor that all illustrated operations must be performed (some operations can be optional). As appropriate, multitasking or parallel-processing (or a combination of multitasking and parallel-processing) can be performed.

What is claimed is:

1. A smart broadcast device, comprising:
    a device body having a first surface and a lower surface joined along a common edge at an acute angle, the first surface comprising a payment graphic code;
    a transceiver operable to maintain a persistent network connection, wherein the persistent network connection comprises a persistent wireless network connection, a persistent wired network connection, or both a persistent wireless connection and persistent wired connection with a payment service provider;
    a processor operable to
        query a binding status between the smart broadcast device and a user account registered with the payment service provider,
        receive, from the transceiver, an external trigger signal sent by the payment service provider through the persistent network connection, and
        generate a control signal for broadcasting a payment result audio; and
    a speaker operable to output the payment result audio upon receiving the control signal from the processor.

2. The smart broadcast device according to claim 1, wherein
    the first surface comprises a display screen configured to display the payment graphic code.

3. The smart broadcast device according to claim 1, wherein
    a printout of the payment graphic code is attached to the first surface.

4. The smart broadcast device according to claim 1, wherein
    the acute angle between the first surface and the lower surface is between 20 degrees to 70 degrees.

5. The smart broadcast device according to claim 1, wherein
    speaker holes of the speaker are on opposite sides of the payment graphic code on the first surface.

6. The smart broadcast device according to claim 1, further comprising an LED status indicator operable to emit a light upon receiving a light emitting control signal from the processor.

7. The smart broadcast device according to claim 6, wherein the LED status indicator is further operable to emit the light in different colors each indicative of (i) the binding status between the smart broadcast device and the user account registered with the payment service provider, or (ii) a status of the persistent network connection with the payment service provider.

8. The smart broadcast device according to claim 1, further comprising one or more volume adjustment buttons for use in adjusting a volume of the payment result audio outputted by the speaker.

9. The smart broadcast device according to claim 1, further comprising a Wi-Fi probe operable to search for end-user device information, wherein
  the processor is further operable to encapsulate, according to a predetermined protocol, the end-user device information that is detected by the Wi-Fi probe, and report the end-user device information to the payment service provider by using the transceiver.

10. The smart broadcast device according to claim 1, further comprising an NFC transceiver operable to
  search for nearby NFC-enabled end-user devices, and
  upon having detected a nearby NFC-enabled end-user device, send information associated with the payment graphic code to the detected nearby NFC-enabled end-user device through NFC communication.

* * * * *